(12) United States Patent
Miyazaki

(10) Patent No.: US 7,517,706 B2
(45) Date of Patent: Apr. 14, 2009

(54) METHOD FOR EVALUATING QUALITY OF SEMICONDUCTOR SUBSTRATE AND METHOD FOR MANUFACTURING SEMICONDUCTOR SUBSTRATE

(75) Inventor: Morimasa Miyazaki, Saga (JP)

(73) Assignee: Sumco Corporation, Tokyo (JP)

( * ) Notice: Subject to any disclaimer, the term of this patent is extended or adjusted under 35 U.S.C. 154(b) by 181 days.

(21) Appl. No.: 11/753,795

(22) Filed: May 25, 2007

(65) Prior Publication Data

US 2008/0020497 A1    Jan. 24, 2008

(30) Foreign Application Priority Data

Jul. 21, 2006    (JP) .............................. 2006-199018

(51) Int. Cl.
*H01L 21/66* (2006.01)

(52) U.S. Cl. .......................................... 438/14; 438/17

(58) Field of Classification Search ...................... 438/5, 438/14, 17
See application file for complete search history.

(56) References Cited

U.S. PATENT DOCUMENTS

| 5,946,543 | A | * | 8/1999 | Kimura et al. .................. 438/14 |
| 7,009,714 | B2 | * | 3/2006 | Ohmoto et al. ............. 356/504 |
| 2004/0106217 | A1 | * | 6/2004 | Higgs ............................ 438/5 |

FOREIGN PATENT DOCUMENTS

JP    2000193597    7/2000

OTHER PUBLICATIONS

English language Abstract of JP 2000-193597.
U.S. Appl. No. 11/564,374 to Miyazaki et al., which was filed on Nov. 29, 2006.
U.S. Appl. No. 11/695,699 to Yamashita, which was filed on Apr. 3, 2007.

* cited by examiner

*Primary Examiner*—Kiesha L Rose
*Assistant Examiner*—Christine Enad
(74) *Attorney, Agent, or Firm*—Greenblum & Bernstein, P.L.C.

(57) ABSTRACT

Methods for evaluating a quality of a semiconductor substrate. In one aspect, etching a surface of the semiconductor substrate by dry-etching, detecting bright points on the surface of the etched surface with a foreign matter inspection device, and evaluating the quality of the semiconductor substrate based on the number and/or distribution pattern of the detected bright points are included. In another aspect, etching a surface of the semiconductor substrate by dry-etching, detecting bright points on the surface of the etched surface with a foreign matter inspection device, and evaluating the quality of the semiconductor substrate are included, and the evaluated quality is a type of metal contaminant contained in the substrate, and the type of metal contaminant is identified by conducting elemental analysis of the detected bright points.

16 Claims, 4 Drawing Sheets

METHOD FOR EVALUATING QUALITY OF SEMICONDUCTOR SUBSTRATE AND METHOD FOR MANUFACTURING SEMICONDUCTOR SUBSTRATE

CROSS-REFERENCE TO RELATED APPLICATIONS

This application claims a benefit of priority under 35 USC 119 to Japanese Patent Application No. 2006-199018 filed on Jul. 21, 2006, which is expressly incorporated herein by reference in its entirety.

BACKGROUND OF THE INVENTION

1. Field of the Invention

The present invention relates to a method for evaluating a quality of a semiconductor substrate, and more particularly, to a method for evaluating metal contamination within the substrate. The present invention further relates to a method for manufacturing a semiconductor substrate, making it possible to provide high-quality semiconductor substrates by identifying a non-defective product using the above method for evaluating a quality of a semiconductor substrate.

2. Discussion of the Background

Inspection methods involving observing bright points on a surface of a semiconductor substrate that are detected by a foreign matter inspection device have been proposed as methods for evaluating the quality of silicon epitaxial wafers, mirror-finished wafers and the like. In these inspection methods, surface particles, crystal originated particles (COP), dislocations, and the like, as well as various surface pits due to the crystal quality of the substrate, are detected as bright points. Since particles on a substrate are observed as protrusions and surface pits are observed as indentations, the causes of bright points resulting from particles and surface pits can be identified to a certain degree.

In mirror-finished wafers, metal ions contained in the slurry used for mirror polishing diffuse into the wafer during the mirror polishing process, creating a problem by contaminating the bulk near the surface. Wafers that have been contaminated by metal in this fashion develop surface crystal defects and surface roughness, compromising quality. Thus, identification of the elements of the various metal impurities present in the bulk near the surface of a semiconductor substrate provides clues to discovery of causes thereof, and thus relates to improvement of the manufacturing process. However, since the crystal defects and surface roughness caused by metal contamination do not appear in the form of protrusions or indentations on the surface of the substrate, they are normally not detected as bright points during inspection by foreign matter inspection devices, and present a risk of a defective substrate being shipped as a non-defective product.

Accordingly, a method has been proposed for identifying metal contaminants in the bulk near the substrate surface by observing, with a foreign matter inspection device, the shape of bright points on the substrate surface following cleaning and comparing this shape to the shapes of bright points on a cleaned reference wafer into which known heavy metals have been diffused. Such a method is described, for example, in Japanese Unexamined Patent Publication (KOKAI) No. 2000-193597, which is expressly incorporated herein by reference in its entirety. However, this method involves a complex process requiring the observation of the shapes of various bright points and their comparison to the shapes of bright points on the reference wafer. There are thus problems in that evaluation is time-consuming and the method lacks practicality.

SUMMARY OF THE INVENTION

An aspect of the present invention provides for a highly practical method of evaluating the quality of semiconductor substrates.

An aspect of the present invention relates to a process for evaluating a quality of a semiconductor substrate. The process includes etching a surface of the semiconductor substrate using dry-etching, detecting bright points on the surface of the etched surface with a foreign matter inspection device, and evaluating the quality of the semiconductor substrate based on the number and/or distribution pattern of the detected bright points. The evaluated quality may be determined in terms of presence or absence and/or degree of metal contamination.

The process further includes identifying a type of metal contaminant contained in the substrate by conducting elemental analysis of the detected bright points. The elemental analysis may be conducted by a scanning electron microscope or transmission electron microscope, and an energy-dispersion X-ray spectroscopy.

According to the exemplary process, the dry-etching may be conducted on the surface of the semiconductor substrate that has been subjected to thermal treatment. The thermal treatment may be conducted at a temperature ranging from approximately 100° C. to approximately 1,200° C.

Further, the dry-etching may be conducted after an oxide film has been formed on the surface of the semiconductor substrate and then stripped away. The semiconductor substrate may be a silicon semiconductor wafer, the surface of which has been mirror finished.

A further aspect of the present invention relates to a process for evaluating a quality of a semiconductor substrate. The process includes etching a surface of the semiconductor substrate by dry-etching, detecting bright points on the surface of the etched surface with a foreign matter inspection device, and evaluating the quality of the semiconductor substrate. The evaluated quality may be a type of metal contaminant contained in the substrate, and the type of metal contaminant may be identified by conducting elemental analysis of the detected bright points. The elemental analysis may be conducted by a scanning electron microscope or a transmission electron microscope, and an energy-dispersion X-ray spectroscopy.

The dry-etching may be conducted on the surface of the semiconductor substrate that has been subjected to thermal treatment. The thermal treatment may be conducted at a temperature ranging from approximately 100° C. to approximately 1,200° C.

Further, the dry-etching may be conducted after an oxide film has been formed on the surface of the semiconductor substrate and then stripped away. The semiconductor substrate may be a silicon semiconductor wafer, the surface of which has been mirror finished.

A further aspect of the invention relates to a method of manufacturing a semiconductor substrate. The method includes preparing a product lot of semiconductor substrate comprising plural semiconductor substrates, extracting at least one semiconductor substrate from the lot, and evaluating the quality of the semiconductor substrate that has been extracted. The method further includes, when the semiconductor substrate that has been extracted is determined as a nondefective product in the quality evaluation process, supplying, as a finished product, a semiconductor substrate comprised in the lot from which the semiconductor substrate that was determined as a nondefective product has been extracted. The evaluation of the extracted semiconductor substrate is conducted by the process for evaluating a quality of a semiconductor substrate according to the present invention.

The present invention permits ready and accurate identification of the type of metal contaminant contained in the substrate. Accordingly, high-quality substrate products can be provided.

Other exemplary embodiments and advantages of the present invention may be ascertained by reviewing the present disclosure and the accompanying drawings.

BRIEF DESCRIPTION OF THE DRAWINGS

The present invention will be described in the following text by the exemplary, non-limiting embodiments shown in the figures, wherein.

Figure 1:
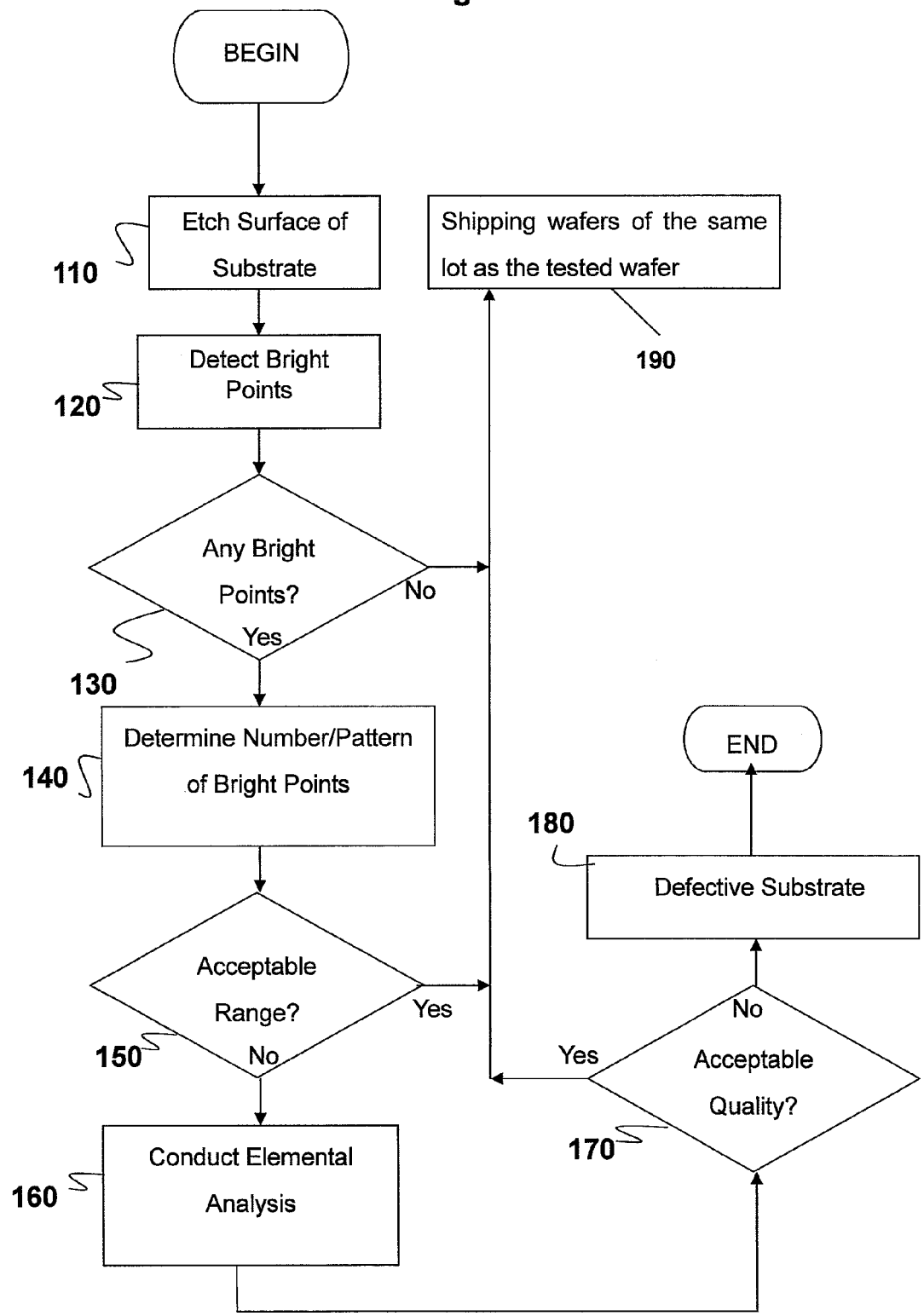
FIG. 1 shows a flow diagram according to a process for evaluating a quality of a semiconductor substrate.

The following preferred specific embodiments are, therefore, to be construed as merely illustrative, and not limitative of the remainder of the disclosure in any way whatsoever. In this regard, no attempt is made to show structural details of the present invention in more detail than is necessary for the fundamental understanding of the present invention, the description taken with the drawings making apparent to those skilled in the art how the several forms of the present invention may be embodied in practice.

According to an aspect of the present invention, two methods are provided for evaluating a quality of a semiconductor substrate. Both methods include etching a surface of the semiconductor substrate and detecting bright points on the surface of the etched surface with a foreign matter inspection device, wherein the etching is conducted by dry-etching. Bright points detected on the surface of a substrate following wet-etching may be traces where the bright points have been removed, that is, become indentations. In dry-etching, the substrate (for example, silicon in the case of a silicon substrate) around a bright point is etched, and the bright point itself tends to remain without being etched.

In the first method (referred to as "Method 1" hereinafter), the quality of the semiconductor substrate is evaluated based on the number of bright points detected and/or a distribution pattern of the detected bright points. In the second method (referred to as "Method 2" hereinafter), the quality is evaluated by elemental analysis of the bright points that have been detected to identify the type of metal contaminant contained in the substrate. Method 1 and Method 2 are not mutually exclusive, but may be applied individually or in a single process.

Method 1 permits the evaluation of whether or not metal contaminants are present, and/or to what degree they are present, on the substrate surface and/or in the vicinity of the surface based on the number of bright points detected, and/or the distribution pattern of the detected bright points, in the substrate surface following dry-etching. This is possible because dry-etching does not cause metal contaminants present on the substrate surface or in the vicinity of the surface to drop out of the substrate; they tend to remain in the etched surface, even after etching.

Method 2 permits identification of the type of metal contaminant contained in the substrate. This is possible because etching the substrate by dry-etching does not cause metal contaminants in the substrate to drop out of the substrate; they tend to remain in the etched surface, even after etching. Exposed metal impurities remaining in the etched surface are detected as bright points by a foreign matter inspection device. Elemental analysis of the bright points detected then permits ready and accurate identification of the type of metal contaminants. Accurate identification of the type of metal contaminants is extremely useful in determining causes of contamination in the manufacturing process and in improving manufacturing steps.

The semiconductor substrate that is subjected to quality evaluation may be, for example, a silicon epitaxial wafer, a silicon wafer product obtained by mirror finishing the surface of a silicon wafer, a wafer product obtained by heat treating, e.g., in a hydrogen or argon atmosphere, a silicon wafer with a mirror-finished surface, or the like. The method of evaluating a quality of the semiconductor substrate is particularly effective for identifying the type of the metal contaminants present in the bulk near the substrate surface that result from diffusion into the substrate of metal ions contained in the slurry employed in mirror surface polishing. Accordingly, application of the method of evaluating a quality of the silicon wafers with mirror-finished surfaces is particularly desirable.

Dry-etching may be conducted in both Methods 1 and 2. A known method of dry-etching, such as reactive ion etching (RIE) or plasma etching, may be employed in Method 1 and/or Method 2. Plasma etching may be conducted, for example, with an electron cyclotron resonance (ECR) plasma etcher. The etching depth can be suitably set to evaluate whether metal contaminants are present, or the degree to which they are present, on the substrate surface or in the bulk near the surface. An etching depth of, for example, approximately 0.1 to approximately 0.5 micrometers is desirable. The etching conditions may be suitably set based on the desired etching depth.

While a surface of the substrate that is being evaluated for a quality of the substrate may be directly dry-etched, it is desirable to subject the substrate surface to a thermal treatment before etching. The thermal treatment can cause metal impurities contained in the bulk to migrate to the vicinity of the surface, permitting identification of the type of the metal contaminants in the bulk with a low level of etching.

The conditions employed in the thermal treatment are desirably set based on the degree of substrate contamination. For example, the temperature of the thermal treatment may be in a range from approximately 100° C. to approximately 1,200° C., and the duration of the thermal treatment may be from approximately 5 minutes to approximately 2 hours. The thermal treatment is desirably conducted in a non-oxidizing environment such as a nitrogen, an argon, or a hydrogen atmosphere, although it is appreciated by those of skill in the art that other suitable environments may be used in alternative embodiments.

According to an aspect of the present invention, dry-etching can be conducted after an oxide film has been formed on the surface of the semiconductor substrate being evaluated and then stripped away. Thus, traces of indentations, where contaminants have been removed during stripping, remain. This is advantageous in that, since the size of the indentations is increased by dry-etching, the detection of bright points by the foreign matter inspection device is facilitated.

The oxide film can be formed, for example, by dry or wet oxidization at about 800° C. to about 1,000° C. The oxide film that is formed can be stripped away with, for example, an aqueous solution of hydrofluoric acid. The concentration of the aqueous solution of hydrofluoric acid should be, for example, between approximately 0.5 to approximately 5 percent of the volume.

An exemplary quality evaluation process by Method 1 and/or Method 2 is described in greater detail below, with reference to FIG. 1.

Referring to FIG. 1, at step 110, a surface of a substrate is dry-etched, for example, in the manner set forth above. At step 120, the process detects bright points on the substrate that has been dry-etched. If bright points are not detected on the substrate ("No" at step 130), the process to step 190.

If bright points are detected on the substrate ("Yes" at step 130), the process determines a number and/or distribution pattern of the detected bright points at step 140. If the number and/or distribution pattern of the detected bright points is determined at step 150 to be within a predetermined tolerance range ("Yes" at step 150), the process to step 190.

If the number and/or distribution pattern of the detected bright points is determined not to be within the predetermined tolerance range ("No" at step 150), the process determines whether metal contamination is present, and/or the degree of such contamination at step 160. The determination is performed by elemental analysis of the bright points that are detected. The elemental analysis may also identify the type of metal contaminants contained in the substrate.

At step 170, the process determines whether the contamination and/or the degree of such contamination is within an a predetermined contamination range and/or type of contaminants. If a determination is made that the contamination and/or the degree of such contamination is not within the predetermined range and/or type of contaminants ("No" at step 170), the process evaluates the quality of the substrate to be defective at step 180 and wafers of the same lot as the tested wafer can not be shipped. Otherwise wafers of the same lot as the tested wafer can be shipped at step 190.

The exemplary process permits the evaluation of whether or not metal contaminants are present, and/or the degree to which they are present, on the substrate surface and/or in the vicinity of the surface. For example, the larger the number of bright points detected, the severer the metal contamination. Further, when an abnormal distribution pattern is exhibited, with bright points concentrated in one portion of the surface, a determination of metal contamination can be made. Still further, the causes of contamination can be inferred from the distribution pattern of bright points. For example, when bright points are distributed in a concentric circular pattern, contamination during drawing of the crystal can be inferred. When a characteristic pattern is present around the perimeter, contamination from the boat during thermal treatment or contamination due to contact with the inspection device can be inferred.

In Method 1, as in Method 2, described further below, elemental analysis of bright points that are detected can be conducted to identify the type of metal contaminants contained in the substrate.

In Method 2, bright points detected by a foreign matter inspection device on the substrate surface following dry-etching are subjected to elemental analysis to identify the type of metal contaminants contained in the substrate. This elemental analysis can be conducted by observing the bright points by scanning electron microscope (SEM) or transmission electron microscope (TEM), and conducting energy-dispersion X-ray spectroscopy at the bright points. Such elemental analysis is possible because dry-etching is employed in Method 2, metal contaminants remain in the substrate following etching, without dropping out.

In Method 2, in addition to the above-described identification of the type of metal contaminants by elemental analysis, it is also possible to evaluate the quality of the substrate based on the number of bright points detected by the foreign matter inspection device, and/or their distribution pattern, in the same manner as in Method 1.

Next is described a process of manufacturing semiconductor substrates according to another aspect of the invention. According to the preferred embodiment, the process of manufacturing a semiconductor substrate includes preparing a product lot of semiconductor substrate having plural semiconductor substrates. The process then extracts at least one semiconductor substrate from the lot for quality evaluation.

The process evaluates the quality of the semiconductor substrate that has been extracted, and when the semiconductor substrate that has been extracted is determined as a nondefective product in the evaluation, the process supplies, as a finished product, a semiconductor substrate comprised in the lot from which the semiconductor substrate determined as a nondefective product has been extracted. The evaluation of the extracted semiconductor substrate is conducted by the process of evaluating a quality of a semiconductor substrate in accordance with the above described aspects of the present invention.

As set forth above, the process of evaluating a quality of a semiconductor substrate permits evaluation of whether metal contaminants are present and/or the degree to which they are present, the identification of the type of metal contaminants, and an inference of the reason(s) for the contamination. Accordingly, by shipping semiconductor substrates of the same lot as semiconductor substrates that have been determined to be nondefective products by this evaluation process, it is possible to provide a high-quality substrate product with high reliability. The criteria for determining nondefective product can be determined by taking into account the physical properties required of the wafer based on the wafer application and the like.

EXAMPLES

The present invention will be further described in detail below based on examples. However, the examples provided below are solely meant to be illustrative and not limiting in any way.

Example 1

A silicon semiconductor wafer, the surface of which had been mirror polished, was dry-etched with a reactive ion etcher to a depth of 0.1 micrometer and then observed with a foreign matter inspection device to determine the pattern distribution of bright points. The etching conditions were as follows: power: 70 W, gas: $SF_6$, pressure: 26.6 Pa, frequency: 13.56 MHz.

Figure 2:
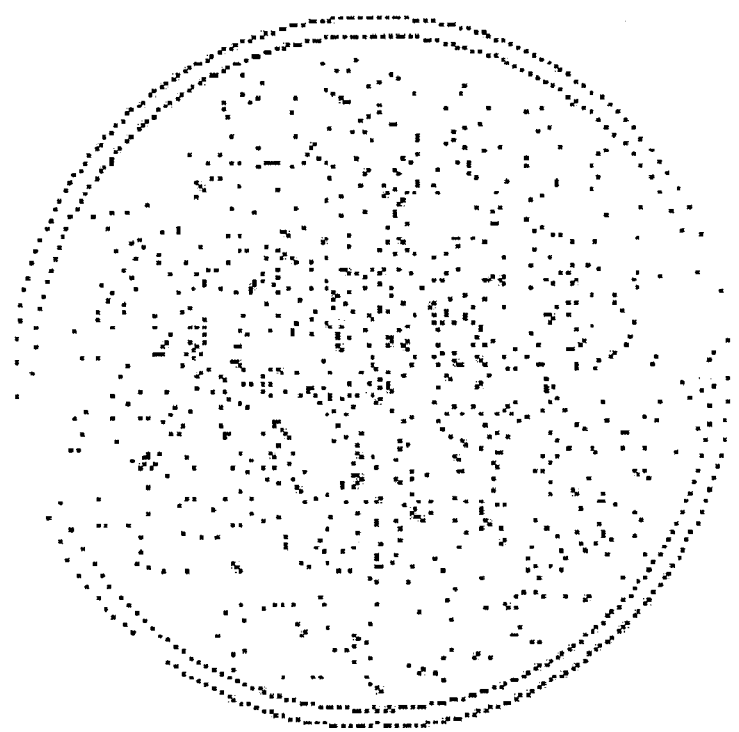
FIG. 2 shows a distribution pattern of bright points on a wafer according to a first example.

FIG. 2 shows an exemplary distribution pattern of the bright points. As shown in FIG. 2, no pattern of abnormal distribution was observed in the wafer evaluated; the wafer was found to be uncontaminated.

Example 2

Figure 3:
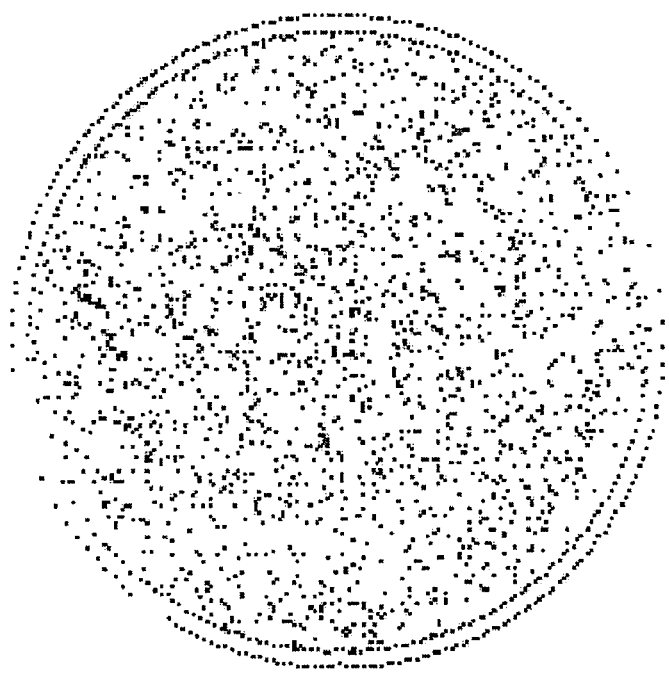
FIG. 3 shows a distribution pattern of bright points on a wafer according to a second example.

With the exception that a silicon semiconductor wafer, the surface of which had been mirror polished, was intentionally contaminated by a spin coater with an aqueous solution of nickel and thermal treated in a nitrogen atmosphere for 10 minutes at 1,000° C. to form nickel silicide in the vicinity of the wafer surface, processing was conducted in the same manner as in Example 1. The distribution pattern of bright points on the surface of the processed wafer was observed with a foreign matter inspection device. The result is shown in FIG. 3. As shown in FIG. 3, the wafer that had been intentionally contaminated with nickel in the vicinity of the surface exhibited a uniform pattern. However, the density of bright points was greater than in the wafer of Example 1.

Figure 4:
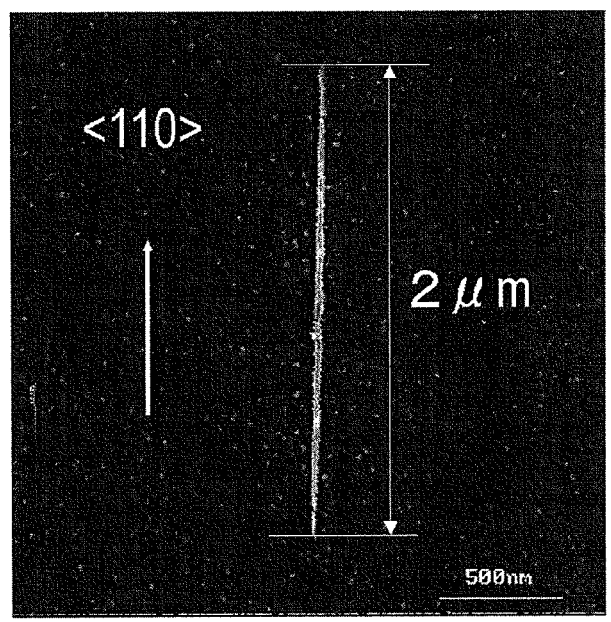
FIG. 4 shows the results of SEM observation according to the second example.
Figure 5:
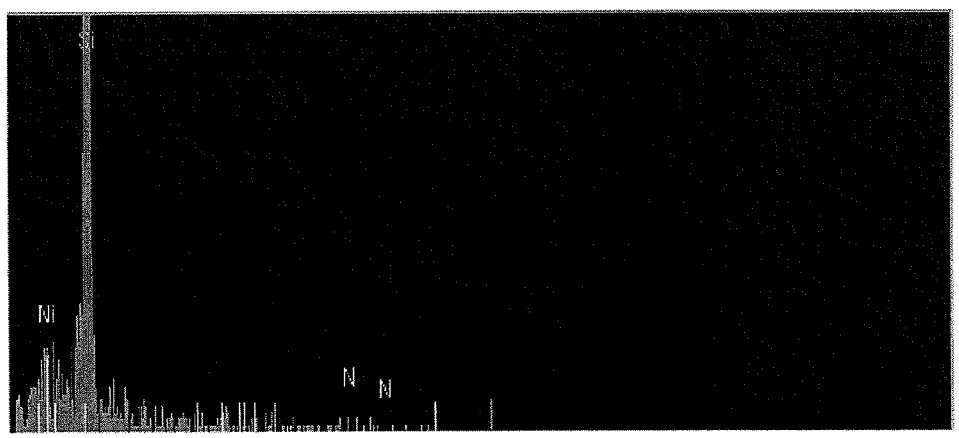
FIG. 5 shows the results of energy-dispersion X-ray spectroscopy according to the second example.

Observation of the increased bright points by SEM revealed protrusions with a <110> orientation, as shown in FIG. 4. Energy-dispersion X-ray spectroscopy detected nickel in the protrusions, as shown in FIG. 5. Based on this information, the protrusions observed were thought to be $NiSi_2$ in the nickel silicide.

Example 3

Figure 6:
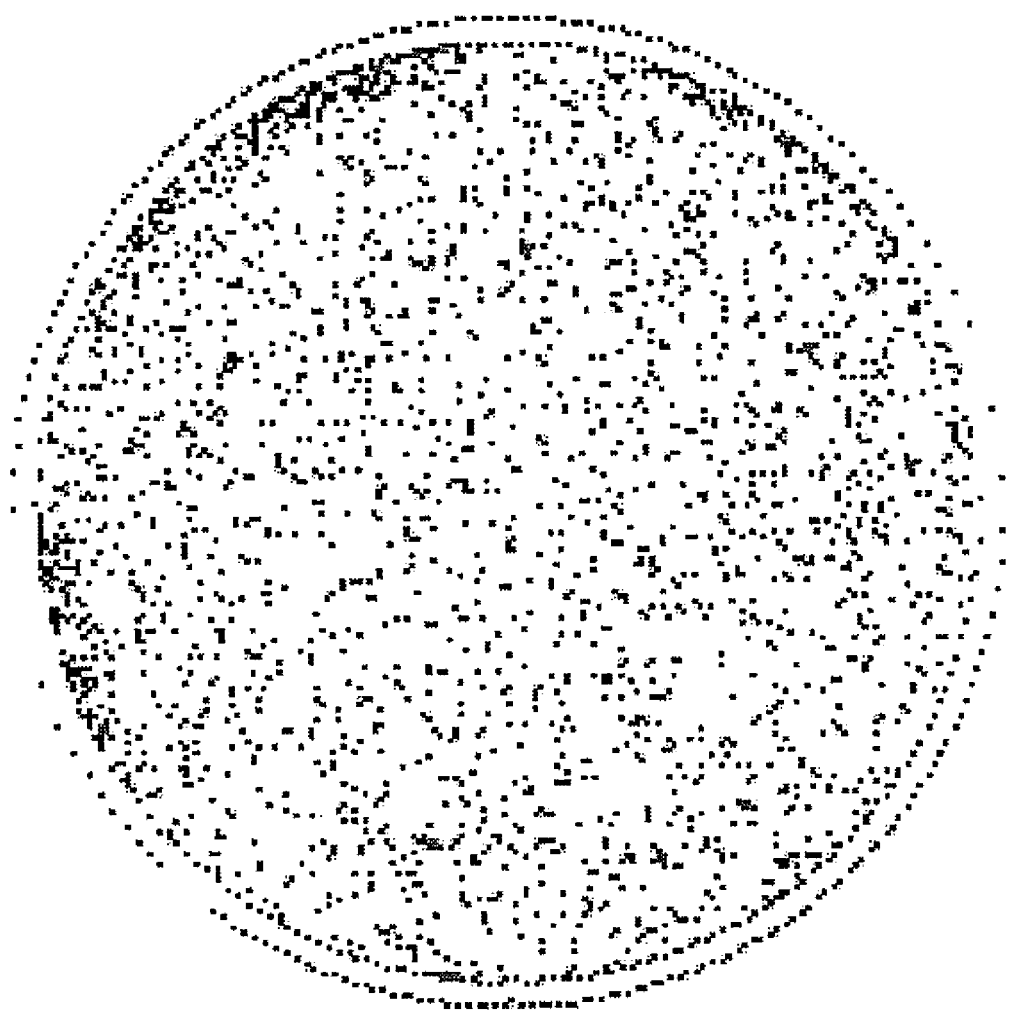
FIG. 6 shows a distribution pattern of bright points on a wafer according to a third example.

With the exception that 50 ppb of copper was mixed into the slurry employed in mirror surface polishing to intentionally form copper silicide on the wafer surface, processing was conducted in the same manner as in Example 1. The pattern of distribution of bright points on the wafer surface following processing was observed with a foreign matter inspection device. The result is shown in FIG. 6. As shown in FIG. 6, the wafer, in which the surface and the bulk in the vicinity of the surface had been intentionally contaminated with copper, exhibited a dense pattern of bright points around its perimeter.

The present invention permits evaluation of whether or not metal contaminants are present and/or the degree to which they are present, and the identification of the type of metal contaminants. The present invention is particularly useful for improving manufacturing processes.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method for evaluating a quality of a semiconductor substrate comprising:
    etching a surface of the semiconductor substrate by dry-etching;
    detecting bright points on the etched surface with a foreign matter inspection device; and
    evaluating the quality of the semiconductor substrate based on a number and/or a distribution pattern of the detected bright points.

2. The method for evaluating a quality of a semiconductor substrate according to claim 1, wherein the evaluated quality is presence, an absence or a degree of metal contamination.

3. The method for evaluating a quality of a semiconductor substrate according to claim 1, further comprising:
    conducting an elemental analysis of the detected bright points; and
    identifying a type of metal contaminant contained in the substrate based on the elemental analysis.

4. The method for evaluating a quality of a semiconductor substrate according to claim 3, wherein said conducting an elemental analysis comprises implementing a scanning electron microscope or a transmission electron microscope, and an energy-dispersion X-ray spectroscopy.

5. The method for evaluating a quality of a semiconductor substrate according to claim 1, wherein said etching is conducted on the surface of the semiconductor substrate that has been subjected to thermal treatment.

6. The method for evaluating a quality of a semiconductor substrate according to claim 5, wherein the thermal treatment is conducted at a temperature ranging from approximately 100° C. to approximately 1,200° C.

7. The method for evaluating a quality of a semiconductor substrate according to claim 1, wherein said etching is conducted after an oxide film has been formed on the surface of the semiconductor substrate and then stripped away.

8. The method for evaluating a quality of a semiconductor substrate according to claim 1, wherein the semiconductor substrate is a silicon semiconductor wafer the surface of which has been mirror finished.

9. A method for evaluating a quality of a semiconductor substrate comprising:
    etching a surface of the semiconductor substrate by dry-etching;
    detecting bright points on the etched surface with a foreign matter inspection device; and
    evaluating the quality of the semiconductor substrate,
    wherein the evaluating comprises determining a type of metal contaminant contained in the substrate by:
    conducting elemental analysis of the detected bright points; and
    identifying the determined type of metal contaminant based on the elemental analysis.

10. The method for evaluating a quality of a semiconductor substrate according to claim 9, wherein said conducting an elemental analysis comprises implementing a scanning electron microscope or a transmission electron microscope, and an energy-dispersion X-ray spectroscopy.

11. The method for evaluating a quality of a semiconductor substrate according to claim 9, wherein said etching is conducted on the surface of the semiconductor substrate that has been subjected to thermal treatment.

12. The method for evaluating a quality of a semiconductor substrate according to claim 11, the thermal treatment being conducted at a temperature ranging from approximately 100° C. to approximately 1,200° C.

13. The method for evaluating a quality of a semiconductor substrate according to claim 9, wherein said etching is conducted after an oxide film has been formed on the surface of the semiconductor substrate and then stripped away.

14. The method for evaluating a quality of a semiconductor substrate according to claim 9, wherein the semiconductor substrate is a silicon semiconductor wafer the surface of which has been mirror finished.

15. A method for manufacturing a semiconductor substrate comprising:
   preparing a product lot of semiconductor substrate comprising plural semiconductor substrates;
   extracting at least one semiconductor substrate from the product lot;
   evaluating the quality of the extracted at least one semiconductor substrate using the method of claim 1; and
   supplying, as a finished product, a semiconductor substrate from the product lot when the extracted at least one semiconductor substrate has been determined as a non-defective product.

16. A method for manufacturing a semiconductor substrate comprising:
   preparing a product lot of semiconductor substrate comprising plural semiconductor substrates;
   extracting at least one semiconductor substrate from the product lot;
   evaluating the quality of the extracted at least one semiconductor substrate using the method of claim 9; and
   supplying, as a finished product, a semiconductor substrate from the product lot when the extracted at least one semiconductor substrate has been determined as a non-defective product.

* * * * *